United States Patent
Kinsho et al.

(10) Patent No.: US 9,481,619 B2
(45) Date of Patent: Nov. 1, 2016

(54) 7-METHYL-3-METHYLENE-7-OCTENYL HALIDE, METHOD FOR PRODUCING THE SAME, AND METHOD FOR PRODUCING 7-METHYL-3-METHYLENE-7-OCTENYL PROPIONATE

(71) Applicant: Shin-Etsu Chemical Co., Ltd., Tokyo (JP)

(72) Inventors: Takeshi Kinsho, Joetsu (JP); Naoki Ishibashi, Joetsu (JP); Yoshiyuki Yumoto, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/974,027

(22) Filed: Dec. 18, 2015

(65) Prior Publication Data

US 2016/0185690 A1    Jun. 30, 2016

(30) Foreign Application Priority Data

Dec. 25, 2014  (JP) .................... 2014-262612

(51) Int. Cl.
| | | |
|---|---|---|
| C07C 67/10 | (2006.01) | |
| C07C 21/19 | (2006.01) | |
| C07C 17/263 | (2006.01) | |
| C07C 17/20 | (2006.01) | |
| C07C 67/11 | (2006.01) | |

(52) U.S. Cl.
CPC ......... *C07C 17/2632* (2013.01); *C07C 17/208* (2013.01); *C07C 21/19* (2013.01); *C07C 67/10* (2013.01); *C07C 67/11* (2013.01)

(58) Field of Classification Search
CPC .... C07C 21/02; C07C 17/2632; C07C 21/14
See application file for complete search history.

(56) References Cited

U.S. PATENT DOCUMENTS

| 3,388,192 A | 6/1968 | Machleidt et al. |
| 4,745,229 A | 5/1988 | Otera et al. |

FOREIGN PATENT DOCUMENTS

GB    2111501 A  *  7/1983

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Ochiai et al. "Iodine(III)-Mediated Allylation of Aromatic Compounds and Alcohols Using Allylmetal (Group IVb) Compounds", *Chem. Pharm. Bull.* 33(1):41:47 (1985).
Gieselmann et al. "Sex Pheromone of the San Jose Scale[1,2]", *J. Chem. Ecol.* 5(6):891-900 (1979).
Anderson et al. "Synthesis of 7-Methyl-3-Methylene-7-Octen-1-YL Propanoate and (Z)-3,7-Dimethyl-2,7-Octadien-1-YL Propanoate, Components of the Sex Pheromone of the San Jose Scale[1]", *J. Chem. Ecol.* 5(6):919-927 (1979).
Weiler et al. "The synthesis of the isomeric components of San Jose scale pheromone—and illustration of a stereospecific synthesis of trisubstituted alkenes", *Can. J. Chem.* 71:1955-1963 (1993).
Weedon et al. "Photoenolisation of Conjugated Esters: Synthesis of a San Jose Scale Pheromone by Partially Regio-Controlled Photochemical Deconjugation[1]", *Tetrahedron Letters* 27(46):5555-5558 (1986).
Zhang et al. "Modification of Wolinsky's Ene-Chlorination", *Chinese Chemical Letters* 2(8):611-612 (1991).
Huaxue Tongbao pp. 40-42 (1994).
Chong et al. "Studies on the Alkylation of 3-Methyl-3-buten-1-ol Dianion: An Efficient Synthesis of 3-Methylene-1-alkanols including a San Jose Scale Sex Pheromone", *J. Org. Chem.* 66:8248-8251 (2001).
Veselovskii et al. "Synthesis of α-Myrcenol Acetate and Propionale from Isobutenylcarbinol", *Izvestiya Akademii Nauk SSSR, Seriya Khimicheskaya* 3:513-516 (1990).
Aldrich et al. "Identification of Presumed Pheromone Blend from Australasian Predaceous Bug, Oechalia schellengergii (Heteroptera: Pentatomidae)", *J. Chem. Ecol.* 22(4):729-738 (1996).
Kozyrkov et al. "A Simple and Efficient Conversion of Tertiary Cyclopropanols to 2-Substituted Allyl Halides", *Synlett* 3:443-446 (2002).

(Continued)

*Primary Examiner* — Paul A Zucker
(74) *Attorney, Agent, or Firm* — Myers Bigel & Sibley, P.A.

(57) ABSTRACT

Provided is a simple, selective and efficient method for producing 7-methyl-3-methylene-7-octenyl propionate and the like. More specifically, provided is, for example, a method for producing 7-methyl-3-methylene-7-octenyl propionate, comprising the steps of: subjecting a nucleophile represented by Formula (1) and an electrophile represented by Formula (2) to a coupling reaction to obtain a 7-methyl-3-methylene-7-octenyl halide represented by Formula (3), and subjecting the 7-methyl-3-methylene-7-octenyl halide (3) to propionyloxylation to obtain the 7-methyl-3-methylene-7-octenyl propionate represented by Formula (4).

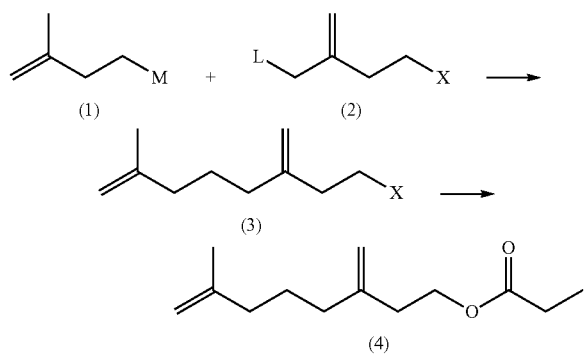

6 Claims, 8 Drawing Sheets

(56) References Cited

OTHER PUBLICATIONS

Kulinkovich et al. "A Convenient Way for the Conversion of Carboxylic Esters into 2-Substituted Allyl Halide", Synthesis 10:1713-1717 (2005).
European Search Report corresponding to European Application No. 15200348 dated Apr. 21, 2016.
Bailey et al. "Pyrolysis of Esters. XXI. 2-Hydroxymethyl-1,2-butadiene[12]", J. Org. Chem. pp. 1975-1978 (1962).
Ferraboschi et at. "Regio- and Enantioselectivity of *Pseudornonas cepacia* Lipase in the Transesterification of 2-Substituted-1,4-Butanediols", *Tetrahedron Asymmetry* 5(4):691-698 (1994).
Li et al. "Approaches to selective isoprenologation via reactions of ($\eta^3$-allyl)Fe(CO)$+_4$ with allyl nucleophiles", *J. Organometalllic Chem.* 402:105-112 (1991).
Tabuchi et al. "Total Synthesis of Alternaric Acid", *Tetrahedron Letters* 34(14):2327-2330 (1993).
Wade et al. "Thermoiytic Rearrangements of 1,1-Cyclopropanedimethanol Disulfonates: Cyclopropylcarbinyl Cations Revisited", *J. Org. Chem,* 58:3140-3147 (1993).
European Search Report corresponding to European Application No. 15200346 dated Apr. 20, 2016.
European Search Report corresponding to European Application No. 15200349 dated Apr. 25, 2016.

\* cited by examiner

7-METHYL-3-METHYLENE-7-OCTENYL HALIDE, METHOD FOR PRODUCING THE SAME, AND METHOD FOR PRODUCING 7-METHYL-3-METHYLENE-7-OCTENYL PROPIONATE

RELATED APPLICATION

This application claims priority from Japanese Patent Application No. 2014-262612, filed Dec. 25, 2014, the disclosure of which is incorporated by reference herein in its entirety.

FIELD AND BACKGROUND OF THE INVENTION

The present invention relates to a method for producing 7-methyl-3-methylene-7-octenyl propionate, which is, for example, a major component of the sex pheromone of *Quadraspidiotus perniciosus* (Comstock) (generic name: San Jose Scale).

The sex pheromones of insects are biologically active substances that are commonly secreted by female individuals and have the function of attracting male individuals. A small amount of the sex pheromone shows strong attractive activities. The sex pheromone has been widely used as means for forecasting insect emergence or for ascertaining regional spread (invasion into a specific area) and as means for controlling an insect pest. As the means for controlling insect pests, control methods called mass trapping, lure and kill (another name: attract and kill), lure and infect (another name: attract and infect), and mating disruption are widely used in practice. To utilize the sex pheromone, economical production of a required amount of the pheromone product is demanded for basic research and also for application.

*Quadraspidiotus perniciosus* (generic name: San Jose Scale, hereinafter abbreviated as "SJS") is widely distributed in the world, damages fruit trees and ornamental trees, especially deciduous fruit trees, and thus is an economically critical insect pest. As for the sex pheromone of SJS, three compounds of 7-methyl-3-methylene-7-octenyl propionate, (Z)-3,7-dimethyl-2,7-octadienyl propionate, and (E)-3,7-dimethyl-2,7-octadienyl propionate have been identified as the active components by Gieselmann et al. (J. Chem. Ecol., 5, 891 (1979)).

These sex pheromone compounds of SJS are isomers to each other, and there is a demand for a selective production method of each compound for basic biological studies and agronomic studies. There is also a strong demand for an efficient production method capable of supplying a sufficient amount of the pheromone product for the purposes of application and practical use.

Examples of the synthesis of 7-methyl-3-methylene-7-octenyl propionate, which is the major component of the sex pheromone of SJS, include the following Syntheses (a) to (f):

Synthesis (a) comprising addition of an organocuprate reagent to alkyne as a key reaction, by Anderson et al. (J. Chem. Ecol., 5, 919 (1979));

Synthesis (b) comprising a one-carbon homologation step of a β-keto ester compound, 7-methyl-3-oxo-7-octenoate, by Weiler et al. (Can. J. Chem., 71, 1955 (1993));

Synthesis (c) comprising photochemical position isomerization of a double bond of an α,β-unsaturated ester to β,γ-unsaturated ester as a key reaction, by Weeden et al. (Tet. Lett., 27, 5555 (1986));

Synthesis (d) comprising exo-methylene formation as a key reaction by reduction of allylic chloride obtained by chlorination involving isomerization of a trisubstituted double bond, by Zhang et al. (Chinese Chemical Letters, 2, 611 (1991), and Huaxue Tongbao, 40, (1994));

Synthesis (e) by alkylation of a dianion of 3-methyl-3-buten-1-ol, by Anderson et al. (J. Chem. Ecol., 5, 919 (1979)) and Chong et al. (J. Org. Chem., 66, 8248 (2001)); and Synthesis (f) which is a nonselective synthesis through an allylic chloride mixture, by Veselovskii et al. (Izvestiya Akademii Nauk SSSR, Seriya Khimicheskaya, 3, 513 (1990)).

SUMMARY OF THE INVENTION

These synthetic methods unfortunately involve a lot of difficulties in order to selectively synthesize 7-methyl-3-methylene-7-octenyl propionate in a high yield on an industrial scale. For example, the difficulties arise from the use of reagents that are expensive or difficult to handle on an industrial scale, including an organolithium reagent such as n-butyllithium and methyllithium in Syntheses (b) and (e), lithium aluminum hydride (LAH) in Syntheses (a), (b) and (d), a stoichiometric amount of an organocuprate reagent in Synthesis (a), a Tebbe reagent in Synthesis (b), and sulfuryl chloride in Synthesis (f). In the synthetic route in which a double bond is intentionally isomerized even by the photochemical isomerization in Synthesis (c) or the isomerization through allylic chloride in Synthesis (d), undesired isomers are unfortunately formed in small amounts as by-products and thus are required to be removed even if the isomerization is achieved with a comparatively high selectivity. The synthesis in Synthesis (f), in which unintended isomers are mixed with a synthetic intermediate, also has significant problems because a target compound is difficult to separate from isomers thereof and the yield is lowered. In Syntheses (a) to (f), intermediates and a target compound are isolated or purified by various types of chromatography, which are difficult to perform on an industrial scale. As described above, the existing syntheses are considered to be very difficult to economically obtain a sufficient amount of the product on an industrial scale.

In view of the above circumstances, an object of the present invention is to provide a simple, selective and efficient production method in order to supply a sufficient amount of 7-methyl-3-methylene-7-octenyl propionate, which is, for example, a major component of the sex pheromone of SJS, the component being required for biological studies, agronomic studies, actual application and utilization, and the like.

As a result of intensive studies, the inventors of the present invention have found that by selecting reagents and conditions that can be easily achieved on an industrial scale, a coupling reaction of a nucleophile having 5 carbon atoms with an electrophile having 5 carbon atoms and having a halogen atom as X can produce a target compound, 7-methyl-3-methylene-7-octenyl halide having 10 carbon atoms with a high selectivity, and the 7-methyl-3-methylene-7-octenyl halide can be converted into a target compound, 7-methyl-3-methylene-7-octenyl propionate, which is a major component of the sex pheromone of SJS, and have completed the present invention.

In an aspect of the present invention, there is provided a method for producing a 7-methyl-3-methylene-7-octenyl halide, comprising the step of: subjecting a nucleophile represented by Formula (1) and an electrophile represented by Formula (2) to a coupling reaction to obtain the 7-methyl-3-methylene-7-octenyl halide represented by Formula (3).

In another aspect of the present invention, there is provided a method for producing 7-methyl-3-methylene-7-octenyl propionate, comprising the steps of: subjecting a nucleophile (1) and an electrophile (2) to a coupling reaction to obtain a 7-methyl-3-methylene-7-octenyl halide (3), and subjecting the 7-methyl-3-methylene-7-octenyl halide (3) to propionyloxylation to obtain the 7-methyl-3-methylene-7-octenyl propionate represented by Formula (4).

In still another aspect of the present invention, there is provided a 7-methyl-3-methylene-7-octenyl halide represented by Formula (3).

In the reaction equation shown in FIG. 1, M represents a cationic moiety, X represents a halogen atom, and L represents a leaving group.

According to the present invention, 7-methyl-3-methylene-7-octenyl propionate can be selectively and efficiently synthesized through a useful intermediate, a 7-methyl-3-methylene-7-octenyl halide, starting from two building blocks each having 5 carbon atoms which can be comparatively easily synthesized as raw materials.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

Figure 1:
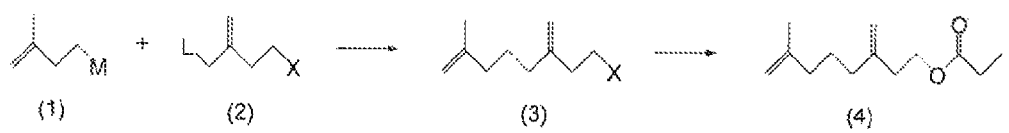
FIG. 1 presents a reaction equation in a retrosynthetic analysis.
Figure 2:
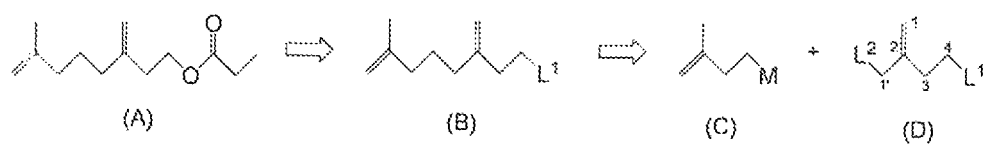
FIG. 2 presents a reaction equation in a retrosynthetic analysis.

The inventors of the present invention have considered the synthetic route shown in FIG. 2 in order to synthesize 7-methyl-3-methylene-7-octenyl propionate (A), which is a target major component of the sex pheromone of SJS. In other words, if a compound (B) having a leaving group $L^1$ at the 1-position, such as a 7-methyl-3-methylene-7-octenyl halide as an intermediate, can be synthesized, it is considered that the compound (B) can be converted into a target propionate compound (A) through the $S_N2$ reaction (bimolecular nucleophilic substitution reaction) of replacing the leaving group $L^1$ with a propionate. It is also considered from the viewpoint of easy availability and cost efficiency of raw materials that the intermediate (B) having 10 carbon atoms can be straightforwardly, efficiently synthesized if two building blocks each having 5 carbon atoms in the reaction equation below can be used to form a bond, that is, if a nucleophile (C) and an electrophile (D) having two leaving groups $L^1$ and $L^2$ and having 5 carbon atoms can undergo a coupling reaction in such a manner that $L^2$ is eliminated.

In the reaction equation shown in FIG. 2, the hollow arrows represent transformation in a retrosynthetic analysis, $L^1$ and $L^2$ represent leaving groups, M represents a cationic moiety, and the small numeric characters attached on carbons of the compound (D) represent the position numbers of the carbons.

Figure 3:
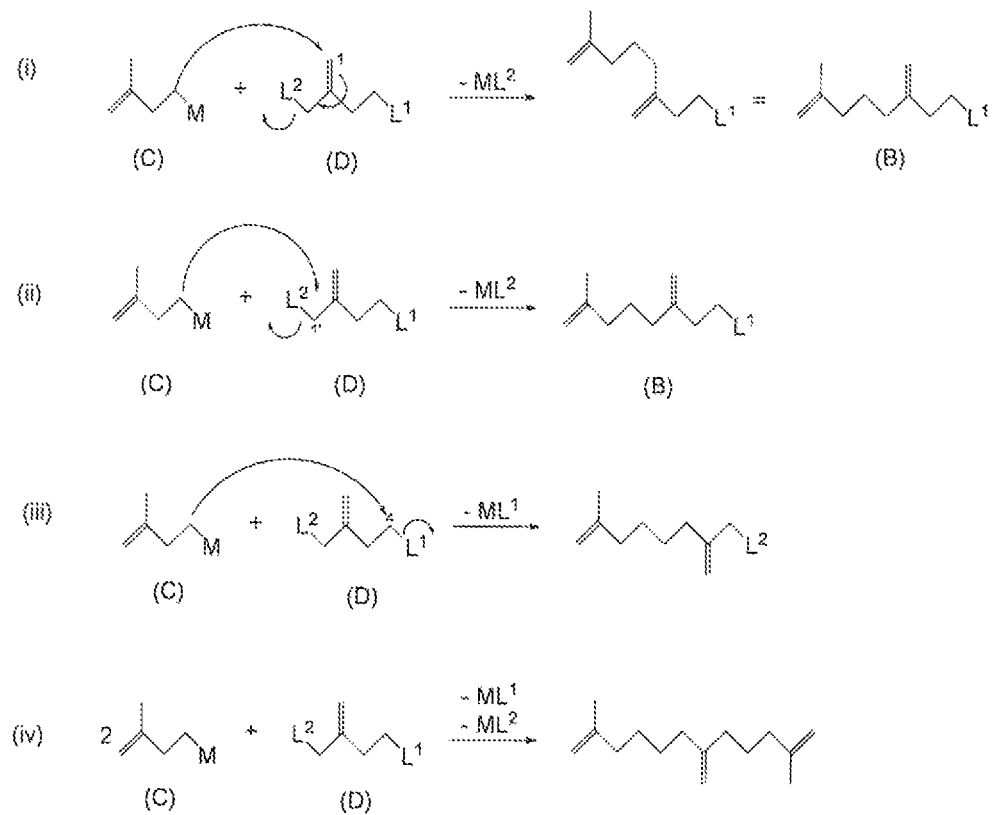
FIG. 3 presents a reaction scheme in a retrosynthetic analysis (i) in which the carbon at the 1-position of the compound (D) is reacted, the reaction scheme (ii) in which the carbon at the 1'-position is reacted, the reaction scheme (iii) in which the carbon at the 4-position is reacted, and the reaction scheme (iv) in which both the carbons at the 1- or 1'-position and at the 4-position are reacted.

In the retrosynthetic analysis, the reaction sites of the electrophile compound (D) capable of forming a carbon-carbon bond with the nucleophile compound (C) can be the carbons at the 1-position, the 1'-position, and the 4-position. Shown in FIG. 3 are the reaction scheme (i) in which the carbon at the 1-position of the compound (D) is reacted, the reaction scheme (ii) in which the carbon at the 1'-position is reacted, the reaction scheme (iii) in which the carbon at the 4-position is reacted, and the reaction scheme (iv) in which both the carbons at the 1- or 1'-position and at the 4-position are reacted.

In the reaction scheme (i), a substitution reaction involving allylic rearrangement that is called an $S_N2'$ reaction occurs at the carbon at the 1-position. In the reaction scheme (ii), a nucleophilic attack occurs at the carbon at the 1'-position to lead to the $S_N2$ reaction, and $L^2$ is eliminated to give the product (B). Accordingly, in each scheme, the same target product (B) is expected to be obtained through the elimination of $L^2$.

On the other hand, in the reaction scheme (iii), it is supposed that a nucleophilic attack occurs at the carbon at the 4-position and $L^1$ is eliminated to give a product that has 10 carbon atoms and differs from the target intermediate (B). In the reaction scheme (iv), it is supposed that two coupling reactions involving the elimination of both $L^1$ and $L^2$ proceed to give a product that has 15 carbon atoms and differs from the target intermediate (B).

As described above, regarding the coupling reaction (the reaction at the carbon at the 1-position or 1'-position) in which the leaving group $L^2$ of the compound (D) as an electrophile is eliminated, and the coupling reaction (the reaction at the carbon at the 4-position) in which the leaving group $L^1$ is eliminated, only the former coupling reaction is preferably, selectively allowed to proceed for the purpose. In the synthetic strategy, $L^1$ and $L^2$ in the compound (D) differ in the substitution positional relation with regard to the double bond. More specifically, $L^2$ is at an allylic position, while $L^1$ is at a homoallylic position. It has thus been considered that the selectivity can be achieved by selecting the types of $L^1$, $L^2$ and M, and reaction conditions.

As a result of repeated studies based on the above consideration, an efficient synthesis having an intended high selectivity is achieved. Embodiments of the present invention will now be described in detail. It should not be construed that the present invention is limited to or by them.

According to the invention, a 7-methyl-3-methylene-7-octenyl halide (3) can be synthesized by a coupling reaction between a nucleophile (1) and an electrophile (2), represented in the following reaction equation. In the reaction equation, M represents a cationic moiety, X represents a halogen atom, and L represents a leaving group. The halogen atom includes chlorine, bromine and iodine.

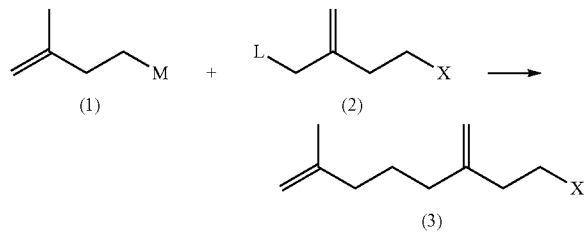

The nucleophile (1) can be exemplified by an organometallic reagent containing a group I or group II metal element or a transition metal element.

Examples of the organometallic reagent containing a group I or group II metal element preferably include an organolithium reagent such as 3-methyl-3-butenyllithium, and an organomagnesium reagent such as a Grignard reagent and a 3-methyl-3-butenylmagnesium halide from the viewpoint of reactivity, selectivity, ease in preparation, and the like.

The organometallic reagent containing a transition metal element may be prepared through a metal exchange reaction using a stoichiometric amount (1 mol) or more of a transition metal compound per mol of the organolithium reagent or the organomagnesium reagent, or may be produced in situ from the organolithium reagent or the organomagnesium reagent in the presence of a transition metal compound catalyst. Examples of the transition metal compound can include a transition metal compound containing copper, iron, nickel, palladium, zinc, silver, or the like. Particularly preferred is a copper compound such as copper(I) chloride, copper(I) bromide, copper(I) iodide, copper(I) cyanide, copper(I) oxide, copper(II) chloride, copper(II) bromide, copper(II) iodide, copper(II) cyanide, copper(II) oxide, and dilithium tetrachlorocuprate ($Li_2CuCl_4$). The amount of the transition metal compound is from a catalytic amount (0.0001 to 0.999 mol) to a stoichiometric amount (1 mol), or an excess amount (more than 1 mol but not greater than 100 mol). A catalytic amount of the transition metal compound is particularly preferably used.

Specifically, the cationic moiety M in the nucleophile (1) is particularly preferably Li, MgQ, ZnQ, Cu, CuQ, or CuLiQ, wherein Q represents a halogen atom or a 3-methyl-3-butenyl group.

The organometallic reagent used as the nucleophile (1) is typically prepared from a corresponding 4-halo-2-methyl-1-butene in a usual manner. The 4-halo-2-methyl-1-butene is preferably 4-bromo-2-methyl-1-butene or 4-iodo-2-methyl-1-butene, each being liquid at normal temperature, in terms of handleability and costs.

The X in the electrophile (2) is preferably a halogen atom, particularly preferably a bromine atom or a chlorine atom from the viewpoint of selectivity in the coupling reaction for desirably keeping X unreacted, ease in synthesis, and the reactivity of the conversion to the target SJS pheromone compound in the subsequent step.

The L in the electrophile (2) can be appropriately selected from leaving groups capable of undergoing a coupling reaction with the nucleophile (1). Examples of the leaving group include a halogen atom; an alkoxy group having 1 to 5 carbon atoms, such as a methoxy group and an ethoxy group; an acyloxy group such as an acetoxy group, a propionyloxy group, a chloroacetyloxy group, a dichloroacetyloxy group, a trichloroacetyloxy group and a trifluoroacetyloxy group; an alkanesulfonyloxy group such as a methanesulfonyloxy group, a trifluoromethanesulfonyloxy group and a trifluorobutanesulfonyloxy group; and an arenesulfonyloxy group such as a benzenesulfonyloxy group, a p-toluenesulfonyloxy group and a naphthalenesulfonyloxy group. Among these leaving groups, L is preferably a halogen atom or an acyloxy group, particularly preferably a chlorine atom, a bromine atom or an acetyloxy group in terms of selectivity in the coupling reaction for desirably making L reacted, and ease in synthesis.

Specifically, the electrophile (2) can be various compound in combination of X and L and is particularly preferably 4-chloro-2-chloromethyl-1-butene (X=L=Cl), 2-bromomethyl-4-chloro-1-butene (X=Cl, L=Br), 2-bromomethyl-4-bromo-1-butene (X=L=Br), 2-chloromethyl-4-bromo-1-butene (X=Br, L=Cl), 4-chloro-2-methylenebutyl acetate (X=Cl, L=OCOCH$_3$), or 4-bromo-2-methylenebutyl acetate (X=Br, L=OCOCH$_3$). Although details will be described in Examples, in the coupling reaction, 4-chloro-2-chloromethyl-1-butene (X=L=Cl) and 2-bromomethyl-4-bromo-1-butene (X=L=Br) can be used as preferred substrates, suggesting that the leaving group at the allylic position is reacted prior to one at the homoallylic position when the leaving groups are the same. In addition, 2-chloromethyl-4-bromo-1-butene (X=Br, L=Cl) can be used as a preferred substrate, suggesting that the chloro group at the allylic position is reacted prior to the bromo group at the homoallylic position even though a bromo group typically has higher reactivity than a chloro group as the leaving group of a substitution reaction with a nucleophile. These are specifically mentioned to support the validity of the synthetic strategy of the present invention.

Among them, the dihalide can be obtained by subjecting the hydroxy group of 1-(2-haloethyl)cyclopropanol to sulfonylation to obtain a sulfonate such as 1-(2-haloethyl)cyclopropyl methanesulfonate and 1-(2-haloethyl)cyclopropyl p-toluenesulfonate; and treating the sulfonate with a halide salt having Lewis acidity to undergo a reaction involving cyclopropyl-allyl rearrangement (Kulinkovich et al., Synthesis, 2005, 1713). In addition, the obtained dihalide is highly valuable for industrial purposes since it can be converted into dihalide having different halogen atoms or into a corresponding acetoxy derivative.

The electrophile (2) such as the 4-halo-2-halomethyl-1-butene may be isolated and then used for the coupling reaction with the nucleophile (1), but the reaction mixture obtained by the treatment of the sulfonate with the halide having Lewis acidity may be directly used for the coupling reaction with the nucleophile (1) in a one pot manner.

The coupling reaction of the nucleophile (1) with the electrophile (2) is carried out typically in a solvent with optional cooling or heating, for example.

The amounts of the nucleophile (1) and the electrophile (2) used for the coupling reaction can be freely selected in consideration of the types of the substrates, conditions, the reaction yield, and cost efficiency such as the prices of intermediates. The nucleophile (1) is preferably used in an amount of 0.2 to 10 mol, more preferably 0.5 to 2 mol, even more preferably 0.8 to 1.5 mol relative to 1 mol of the electrophile (2).

Examples of the solvent to be used for the coupling reaction preferably include ethers such as diethyl ether, di-n-butyl ether, t-butyl methyl ether, cyclopentyl methyl ether, tetrahydrofuran and 1,4-dioxane. The solvent may be a mixed solvent of one or more ethers with one or more selected from hydrocarbons such as hexane, heptane, benzene, toluene, xylene and cumene; and aprotic polar solvents such as N,N-dimethylformamide (DMF), N,N-dimethylacetamide, N,N-dimethylpropionamide, 1,3-dimethyl-2-imidazolidinone (DMI), dimethyl sulfoxide (DMSO) and hexamethylphosphoric triamide (HMPA). The amount of the solvent is not particularly limited. The amount of the solvent is preferably 0.1 part to 1,000,000 parts, more preferably 1 part to 100,000 parts, even more preferably 10 parts to 10,000 parts relative to 100 parts of the electrophile (2).

As the catalyst to be used for the coupling reaction, a lithium salt such as lithium chloride, lithium bromide and lithium iodide can be used in an amount of 0.0001 to 5 mol relative to 1 mol of the electrophile (2).

The reaction temperature during the coupling reaction is preferably −78° C. to the boiling point temperature of a solvent, more preferably −10° C. to 100° C. The reaction time can be freely selected and is preferably optimized by tracking the progress of the reaction by gas chromatography (GC) or thin-layer chromatography (TLC). Typically, the reaction time is preferably 5 minutes to 240 hours.

If the target intermediate, 7-methyl-3-methylene-7-octenyl halide (3) obtained by the above coupling reaction has sufficient purity, the crude product may be subjected to the subsequent step without treatment, or may be purified by a method appropriately selected from purification methods commonly used in organic synthesis, such as distillation and various types of chromatography. Distillation is particularly preferred from the viewpoint of industrial cost efficiency.

According to the invention, the 7-methyl-3-methylene-7-octenyl halide (3) can also be obtained by a halogenation reaction of converting the hydroxy group of 7-methyl-3-methylene-7-octene-1-ol into a halogen atom. In this case, the halogenation reaction can be carried out by various known methods of converting an alcohol into a halide.

According to the invention, regarding the 7-methyl-3-methylene-7-octenyl halide (3), 7-methyl-3-methylene-7-octenyl bromide (X=Br) can also be synthesized through a halogen exchange reaction from 7-methyl-3-methylene-7-octenyl chloride (X=Cl), while 7-methyl-3-methylene-7-octenyl iodide (X=I) can also be synthesized through a halogen exchange reaction from 7-methyl-3-methylene-7-octenyl chloride (X=Cl) or 7-methyl-3-methylene-7-octenyl bromide (X=Br). This halogen exchange reaction can be carried out by a known method, for example, in which a 7-methyl-3-methylene-7-octenyl halide as the raw material is heated in a solvent together with a halide salt having the same anionic moiety as that of the target halide. The conversion of a halide into another halide may be carried out by advance before the subsequent step. Alternatively, the conversion may be carried out in situ concurrently with the subsequent step in situ, as described later.

Next, the ester formation reaction of converting the 7-methyl-3-methylene-7-octenyl halide (3) obtained as above into a target compound, 7-methyl-3-methylene-7-octenyl propionate (4) will be described. In the reaction equation, X represents a halogen atom.

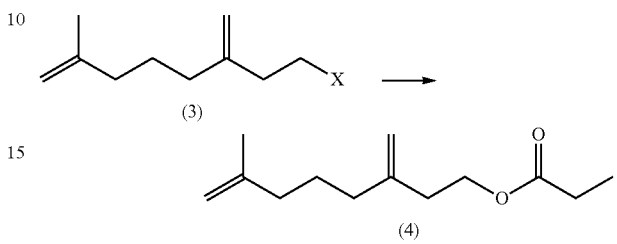

The ester formation reaction is typically carried out by heating the 7-methyl-3-methylene-7-octenyl halide (3) together with a salt of propionic acid in a solvent.

Examples of the propionate salt can include lithium propionate, sodium propionate, potassium propionate, magnesium propionate, calcium propionate, ammonium propionate, tetraalkylammonium propionate and tetraalkylphosphonium propionate. The amount of the propionate salt can be freely selected in consideration of various conditions and is preferably 0.2 to 100 mol, more preferably 1 to 20 mol, even more preferably 1 to 10 mol relative to 1 mol of the 7-methyl-3-methylene-7-octenyl halide (3).

Examples of the solvent to be used for the ester formation reaction include propionic acid; propionic anhydride; propionic acid esters such as methyl propionate, ethyl propionate, n-propyl propionate, n-decyl propionate and benzyl propionate; ethers such as diethyl ether, di-n-butyl ether, t-butyl methyl ether, cyclopentyl methyl ether, tetrahydrofuran and 1,4-dioxane; hydrocarbons such as hexane, heptane, benzene, toluene, xylene and cumene; aprotic polar solvents such as N,N-dimethylformamide (DMF), N,N-dimethylacetamide, N,N-dimethylpropionamide, 1,3-dimethyl-2-imidazolidinone (DMI), dimethyl sulfoxide (DMSO) and hexamethylphosphoric triamide (HMPA). The solvent is used singly or in combination of two or more. The amount of the solvent is not particularly limited. The amount of the solvent is preferably 0.1 parts to 1,000,000 parts, more preferably 1 part to 100,000 parts, even more preferably 10 parts to 10,000 parts relative to 100 parts of the 7-methyl-3-methylene-7-octenyl halide (3).

When 7-methyl-3-methylene-7-octenyl chloride or 7-methyl-3-methylene-7-octenyl bromide is used as the 7-methyl-3-methylene-7-octenyl halide (3) in the ester formation reaction, an iodide salt such as lithium iodide, sodium iodide, potassium iodide, magnesium iodide, calcium iodide, ammonium iodide, tetraalkylammonium iodide, and tetraalkylphosphonium iodide may be added to the reaction system, preferably in an amount of 0.0001 to 5 mol relative to 1 mol of the halide (3), so that the reaction can be carried out through 7-methyl-3-methylene-7-octenyl iodide formed in situ.

In the ester formation reaction, a silver salt such as silver nitrate may also be added preferably in an amount of 0.0001 to 5 mol relative to 1 mol of the 7-methyl-3-methylene-7-octenyl halide (3) and the resulting halide ion may be crystallized and precipitated as a silver salt (silver halide) to accelerate the reaction.

The reaction temperature during the ester formation reaction is preferably 0° C. to the boiling point temperature of a solvent, more preferably 20 to 100° C. The reaction time can be freely selected and is preferably optimized by tracking the progress of the reaction by gas chromatography (GC) or thin-layer chromatography (TLC). Typically, the reaction time is preferably 5 minutes to 240 hours.

As a side reaction of the ester formation reaction, an elimination reaction of a hydrogen halide occurs competitively, and 7-methyl-3-methylene-1,7-octadiene is formed as a by-product. In order to reduce the elimination reaction and to increase the intended substitution reaction (ester formation reaction), various reaction conditions are preferably selected.

The target compound, 7-methyl-3-methylene-7-octenyl propionate (4) obtained by the above ester formation reaction can be isolated by a method appropriately selected from purification methods commonly used in organic synthesis, such as distillation and various types of chromatography. Distillation is particularly preferred from the viewpoint of industrial cost efficiency.

As described above, a simple and efficient method for producing 7-methyl-3-methylene-7-octenyl propionate, which is a product of the sex pheromone of SJS, is provided for product supply in an amount sufficient for application and utilization.

EXAMPLES

The present invention will next be described in further detail with reference to Examples. It should not be construed that the present invention is limited to or by them.

In the following description, as the purities of raw materials and products, the values obtained by gas chromatography (GC) analyses are used and expressed as % GC.

Example 1

Synthesis 1 of 7-methyl-3-methylene-7-octenyl chloride

Figure 4:
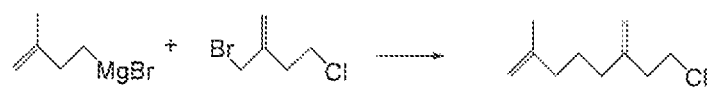
FIG. 4 presents a reaction equation in the synthesis of 7-methyl-3-methylene-7-octenyl chloride.

As shown in FIG. 4, 3-methyl-3-butenylmagnesium bromide is reacted with 2-bromomethyl-4-chloro-1-butene to produce 7-methyl-3-methylene-7-octenyl chloride.

Under a nitrogen atmosphere, a mixture of 34.0 g of 3-methyl-3-butenyl bromide (99.3% GC), 8.5 g of 1,2-dibromoethane to be used for activation of magnesium, and 300 ml of tetrahydrofuran was added dropwise to a mixture of 6.64 g of magnesium and 10 ml of tetrahydrofuran to prepare a Grignard reagent, 3-methyl-3-butenylmagnesium bromide. While being stirred under a nitrogen atmosphere, the Grignard reagent was added dropwise to an ice-cooled mixture of 24.8 g of 2-bromomethyl-4-chloro-1-butene, 160 mg of copper(I) iodide, 240 mg of triethyl phosphite and 250 ml of tetrahydrofuran over 30 minutes for which the temperature was kept at 25° C. or lower. The reaction mixture was stirred for 1 hour while increasing the temperature of the reaction mixture to room temperature. Then the reaction mixture was re-cooled on ice, and subjected to addition of a saturated aqueous ammonium chloride solution for stopping the reaction. The organic phase was separated and then subjected to common work-up of washing, drying and concentration to obtain 29.3 g of 7-methyl-3-methylene-7-octenyl chloride (78% GC, yield 98%).

7-Methyl-3-methylene-7-octenyl chloride

Yellowish Oil
IR (D-ATR): v=3074, 2966, 2937, 1649, 1451, 889 cm$^{-1}$.

$^1$H-NMR (500 MHz, CDCl$_3$): δ=1.54-1.62 (2H, m), 1.72 (3H, s), 1.99-2.05 (4H, m), 2.49 (2H, t, J=7 Hz), 3.61 (2H, t, J=7.5 Hz), 4.68 (1H, s-like), 4.72 (1H, s-like), 4.82 (1H, s-like), 4.87 (1H, s-like) ppm.

$^{13}$C-NMR (125 MHz, CDCl$_3$): δ=22.32, 25.49, 33.32, 37.26, 39.06, 42.76, 110.05, 111.63, 145.52, 145.56 ppm.

GC-MS (EI, 70 eV): 68 (base peak), 81, 95, 109, 119, 129, 144, 157, 172 (M$^+$).

GC-MS (CI, isobutane): 69, 81, 95, 109, 123, 137 (base peak), 145, 159, 173 [(M+H)$^+$].

Example 2

Synthesis 2 of 7-methyl-3-methylene-7-octenyl chloride

Figure 5:
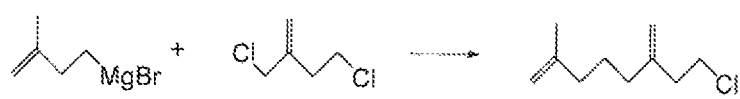
FIG. 5 presents a reaction equation in the synthesis of 7-methyl-3-methylene-7-octenyl chloride.

As shown in FIG. 5, 3-methyl-3-butenylmagnesium bromide is reacted with 4-chloro-2-chloromethyl-1-butene to produce 7-methyl-3-methylene-7-octenyl chloride.

The reaction was carried out in the same manner as in Example 1 except that 7.30 g of 4-chloro-2-chloromethyl-1-butene (94% GC) was used in the place of 2-bromomethyl-4-chloro-1-butene to produce 9.71 g of 7-methyl-3-methylene-7-octenyl chloride (88% GC, quantitative yield). The product was the same as the product in Example 1.

Example 3

Synthesis 1 of 7-methyl-3-methylene-7-octenyl bromide

Figure 6:
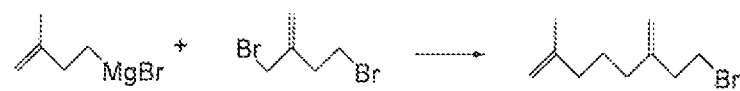
FIG. 6 presents a reaction equation in the synthesis of 7-methyl-3-methylene-7-octenyl bromide.

As shown in FIG. 6, 3-methyl-3-butenylmagnesium bromide is reacted with 4-bromo-2-bromomethyl-1-butene to produce 7-methyl-3-methylene-7-octenyl bromide.

The reaction was carried out in the same manner as in Example 1 except that 7.46 g of 4-bromo-2-bromomethyl-1-butene was used in the place of 2-bromomethyl-4-chloro-1-butene to produce 10.42 g of 7-methyl-3-methylene-7-octenyl bromide (90.2% GC, quantitative yield).

7-Methyl-3-methylene-7-octenyl bromide

Yellowish Oil
IR (D-ATR): v=3075, 2968, 2936, 1647, 1447, 889 cm$^{-1}$.

$^1$H-NMR (500 MHz, CDCl$_3$): δ=1.54-1.62 (2H, quintet-like m), 1.72 (3H, s), 1.98-2.06 (4H, m), 2.58 (2H, t, J=8 Hz), 3.46 (2H, t, J=7.5 Hz), 4.68 (1H, s-like), 4.72 (1H, s-like), 4.81 (1H, s-like), 4.87 (1H, s-like) ppm.

$^{13}$C-NMR (125 MHz, CDCl$_3$): δ=22.34, 25.47, 30.92, 35.16, 37.26, 39.33, 110.07, 111.59, 145.51, 146.32 ppm.

GC-MS (EI, 70 eV): 27, 41, 53, 68, 81 (base peak), 95, 109, 121, 137, 160, 175, 188, 201, 216 (M$^+$).

Example 4

Synthesis 2 of 7-methyl-3-methylene-7-octenyl bromide

Figure 7:
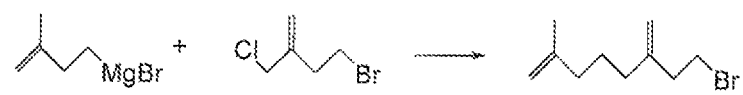
FIG. 7 presents a reaction equation in the synthesis of 7-methyl-3-methylene-7-octenyl bromide.

As shown in FIG. 7, 3-methyl-3-butenylmagnesium bromide is reacted with 2-chloromethyl-4-bromo-1-butene to produce 7-methyl-3-methylene-7-octenyl bromide.

The reaction was carried out in the same manner as in Example 1 except that 1, 2.79 g of 2-chloromethyl-4-bromo-1-butene was used in the place of 2-bromomethyl-4-chloro-1-butene to produce 3.75 g of 7-methyl-3-methylene-7- octenyl bromide (88% GC, quantitative yield). The product was the same as the product in Example 3.

Example 5

Figure 8:
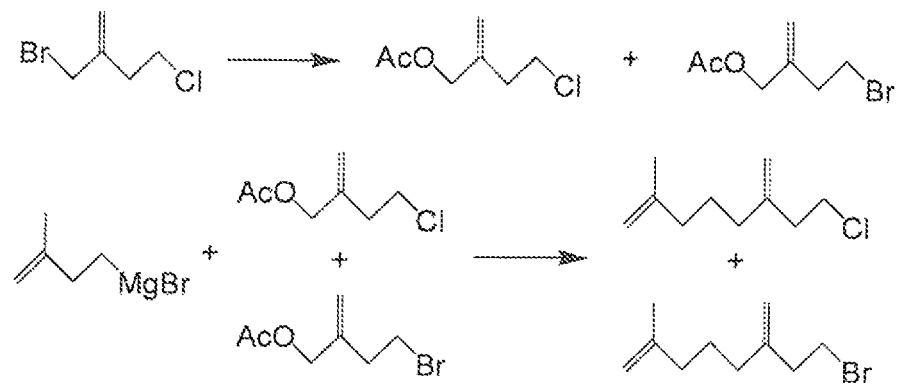
FIG. 8 presents a reaction equation in the synthesis of a mixture of 7-methyl-3-methylene-7-octenyl chloride and 7-methyl-3-methylene-7-octenyl bromide.

Synthesis of Mixture of
7-methyl-3-methylene-7-octenyl chloride and
7-methyl-3-methylene-7-octenyl bromide As shown in FIG. 8, a mixture of 2-methylene-4-chlorobutyl acetate and 2-methylene-4-bromobutyl acetate is obtained from 2-bromomethyl-4-chloro-1-butene in step 5-1, and then a mixture of 7-methyl-3-methylene-7-octenyl chloride and 7-methyl-3-methylene-7-octenyl bromide is obtained from the mixture of 2-methylene-4-chlorobutyl acetate and 2-methylene-4-bromobutyl acetate in step 5-2.
Step 5-1

Under a nitrogen atmosphere, a mixture of 43.2 g of 2-bromomethyl-4-chloro-1-butene, 30.0 g of sodium acetate and 100 g of N,N-dimethylacetamide was stirred at 85° C. for 140 minutes. The reaction mixture was cooled, then poured in water, and extracted with n-hexane. The hexane solution was subjected to the work-up of washing, drying and concentration to obtain 46.85 g of a mixture of 2-methylene-4-chlorobutyl acetate and 2-methylene-4-bromobutyl acetate at 57:43 as a crude product. Next, the products were distilled under reduced pressure to obtain fractions containing 2-methylene-4-chlorobutyl acetate and 2-methylene-4-bromobutyl acetate at mixing ratios of 87:13 to 11:89. The yield of 2-methylene-4-chlorobutyl acetate was 55.4%, the yield of 2-methylene-4-bromobutyl acetate was 33%, and the total yield of two compounds was 88%.

2-Methylene-4-chlorobutyl acetate (74.1% GC)

Colorless Oil
IR (D-ATR): v=1741, 1654, 1440, 1374, 1228, 1029, 915 cm$^{-1}$.
$^1$H-NMR (500 MHz, CDCl$_3$): δ=2.08 (3H, s), 2.54 (2H, t, J=7.3 Hz), 3.63 (2H, t, J=7.3 Hz), 4.53 (2H, s), 5.06 (1H, s-like), 5.18 (1H, s-like) ppm.
$^{13}$C-NMR (125 MHz, CDCl$_3$): δ=20.84, 36.26, 42.22, 66.50, 115.73, 140.00, 170.53 ppm.
GC-MS (EI, 70 eV): 27, 43 (base peak), 53, 71, 83, 102, 120, 133, 147, 162 (M$^+$).

2-Methylene-4-bromobutyl acetate (81.2% GC)

Colorless Oil
IR (D-ATR): v=1741, 1655, 1437, 1374, 1228, 1030, 914 cm$^{-1}$.
$^1$H-NMR (500 MHz, CDCl$_3$): δ=2.08 (3H, s), 2.64 (2H, t, J=7 Hz), 3.48 (2H, t, J=7.3 Hz), 4.54 (2H, s), 5.05 (1H, s-like), 5.18 (1H, s-like) ppm.
$^{13}$C-NMR (125 MHz, CDCl$_3$): δ=20.86, 30.11, 36.48, 66.36, 115.69, 140.69, 170.54 ppm.
GC-MS (EI, 70 eV): 29, 43 (base peak), 55, 72, 84, 126, 144, 168.
Step 5-2

The reaction was carried out in the same manner as in Example 1 except that 7.88 g of a mixture of 2-methylene-4-chlorobutyl acetate and 2-methylene-4-bromobutyl acetate (chloride of 34.1% GC, bromide of 61.9% GC) was used in place of 2-bromomethyl-4-chloro-1-butene to produce 8.95 g of a mixture of 7-methyl-3-methylene-7-octenyl chloride and 7-methyl-3-methylene-7-octenyl bromide (chloride of 28.6% GC, bromide of 51.4% GC, yield 95%). The product was a mixture of the product in Example 1 and the product in Example 3.

Example 6

Synthesis of 7-methyl-3-methylene-7-octenyl iodide

As shown in the following reaction equation, 7-methyl-3-methylene-7-octenyl iodide is obtained from 7-methyl-3-methylene-7-octenyl bromide.

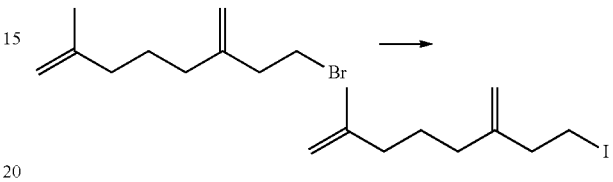

Under a nitrogen atmosphere, a mixture of 9.20 g of 7-methyl-3-methylene-7-octenyl bromide (90.2% GC) obtained in Example 3, 10.0 g of sodium iodide, and 300 ml of acetone was stirred under reflux for 90 minutes and was further stirred at room temperature for 15.5 hours. The reaction mixture was poured in water and extracted with n-hexane. The hexane solution was subjected to the work-up of washing, drying and concentration to obtain 10.82 g of 7-methyl-3-methylene-7-octenyl iodide (90.1% GC, yield 97%).

7-Methyl-3-methylene-7-octenyl iodide

Colorless Oil
IR (D-ATR): v=3074, 2966, 2935, 1647, 1444, 1170, 889 cm$^{-1}$.
$^1$H-NMR (500 MHz, CDCl$_3$): δ=1.54-1.62 (2H, m), 1.72 (3H, s), 2.01 (4H, t-like, J=7.7 Hz), 2.59 (2H, t, J=8 Hz), 3.24 (2H, t, J=7.7 Hz), 4.68 (1H, s-like), 4.72 (1H, s-like), 4.80 (1H, s-like), 4.87 (1H, s-like) ppm.
$^{13}$C-NMR (125 MHz, CDCl$_3$): δ=3.56, 22.35, 25.48, 34.90, 37.29, 40.36, 110.07, 111.21, 145.52, 147.85 ppm.
GC-MS (EI, 70 eV): 27, 41, 67, 81 (base peak), 95, 109, 137, 155, 208, 264 (M$^+$).
GC-MS (CI, isobutane): 69, 81, 95, 109, 123, 137 (base peak), 209, 223, 237, 251, 265 [(M+H)$^+$].

Example 7

Synthesis 1 of 7-methyl-3-methylene-7-octenyl propionate

As shown in the following reaction equation, 7-methyl-3-methylene-7-octenyl propionate is obtained from 7-methyl-3-methylene-7-octenyl chloride.

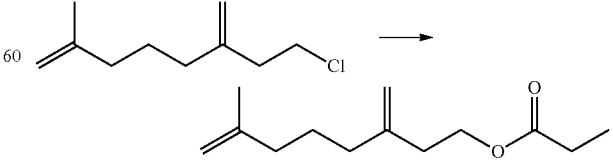

Under a nitrogen atmosphere, a mixture of 28.8 g of 7-methyl-3-methylene-7-octenyl chloride (78% GC)

obtained in Example 1, 19.0 g of sodium propionate, 0.8 g of sodium iodide, and 300 ml of N,N-dimethylformamide was stirred at 80 to 110° C. for 8 hours and was further stirred at room temperature for 14 hours. The reaction mixture was poured in water and extracted with n-hexane. The hexane solution was subjected to the work-up of washing, drying and concentration to obtain a crude product. Next, the crude product was distilled under reduced pressure to obtain 1.94 g of 7-methyl-3-methylene-1,7-octadiene (99% GC, yield 11%) as a by-product through the elimination reaction and 20.14 g of 7-methyl-3-methylene-7-octenyl propionate (95% GC, yield 74%) as the target compound.

7-Methyl-3-methylene-1,7-octadiene

Colorless Oil
IR (D-ATR): ν=3777, 2970, 2937, 1650, 1595, 1449, 1374, 991, 889 $cm^{-1}$.
$^1$H-NMR (500 MHz, $CDCl_3$): δ=1.61-1.69 (2H, m), 1.73 (3H, s), 2.06 (2H, t, J=7.7 Hz), 2.21 (2H, t-like, J=8 Hz), 4.71 (2H, d-like, J=13 Hz), 5.01 (2H, d-like, J=8 Hz), 5.06 (1H, d-like, J=11 Hz), 5.24 (1H, d, J=18 Hz), 6.38 (1H, dd, J=10.7, 17.5 Hz) ppm.
$^{13}$C-NMR (125 MHz, $CDCl_3$): δ=22.37, 26.06, 30.90, 37.62, 109.96, 113.10, 115.64, 138.94, 145.72, 146.32 ppm.
GC-MS (EI, 70 eV): 27, 41, 68, 79 (base peak), 93, 107, 121, 136 ($M^+$).

7-Methyl-3-methylene-7-octenyl propionate

Colorless Oil
IR (D-ATR): ν=3075, 2981, 2938, 1739, 1645, 1462, 1375, 1349, 1182, 1084, 889 $cm^{-1}$.
$^1$H-NMR (500 MHz, $CDCl_3$): δ=1.12 (3H, t, J=7.6 Hz), 1.53-1.61 (2H, m), 1.71 (3H, s), 1.97-2.06 (4H, m), 2.31 (2H, q, J=7.6 Hz), 2.33 (2H, t-like, J=7 Hz), 4.17 (2H, t, J=7.1 Hz), 4.67 (1H, s-like), 4.70 (1H, s-like), 4.77 (1H, s-like), 4.81 (1H, s-like) ppm.
$^{13}$C-NMR (125 MHz, $CDCl_3$): δ=9.10, 22.32, 25.51, 27.56, 34.95, 35.86, 37.29, 62.73, 109.96, 111.18, 145.44, 145.60, 174.41 ppm.
GC-MS (EI, 70 eV): 29, 41, 57 (base peak), 68, 79, 93, 107, 121, 136, 210 ($M^+$).

Example 8

Synthesis 2 of 7-methyl-3-methylene-7-octenyl propionate

As shown in the following reaction equation, 7-methyl-3-methylene-7-octenyl propionate is obtained from 7-methyl-3-methylene-7-octenyl bromide.

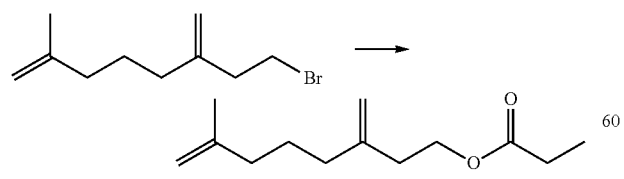

Under a nitrogen atmosphere, a mixture of 3.70 g of 7-methyl-3-methylene-7-octenyl bromide (88% GC) obtained in Example 4, 2.50 g of sodium propionate, and 30 ml of N,N-dimethylacetamide was stirred at 92° C. for 2.5 hours. The reaction mixture was cooled, then poured in water, and extracted with diethyl ether. The diethyl ether solution was subjected to the work-up of washing, drying and concentration to obtain a crude product. The crude product was a mixture of 7-methyl-3-methylene-1,7-octadiene (14% GC, yield 24%) and 7-methyl-3-methylene-7-octenyl propionate (85% GC, yield 85%).

Example 9

Synthesis 3 of 7-methyl-3-methylene-7-octenyl propionate

As shown in the following reaction equation, 7-methyl-3-methylene-7-octenyl propionate is obtained from 7-methyl-3-methylene-7-octenyl iodide.

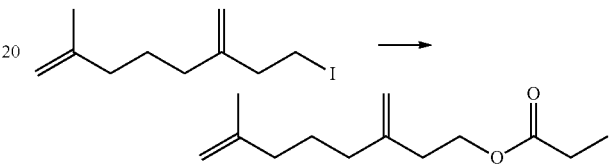

Under a nitrogen atmosphere, a mixture of 10.0 g of 7-methyl-3-methylene-7-octenyl iodide (90.1% GC) obtained in Example 6, 8.00 g of sodium propionate, and 50 ml of N,N-dimethylacetamide was stirred at 90° C. for 4 hours. The reaction mixture was cooled, then poured in water, and extracted with diethyl ether. The diethyl ether solution was subjected to the work-up of washing, drying and concentration to obtain a crude product. The crude product was a mixture of 7-methyl-3-methylene-1,7-octadiene (26% GC, yield 44%) and 7-methyl-3-methylene-7-octenyl propionate (65% GC, yield 70%).

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. A method for producing a 7-methyl-3-methylene-7-octenyl halide, comprising the step of:
subjecting a nucleophile of Formula (1):

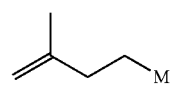

(1)

wherein M is Li, MgQ, Cu, CuQ or CuLiQ, wherein Q is a halogen atom or a 3-methyl-3-butenyl group and an electrophile of Formula (2):

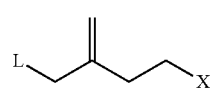

(2)

wherein X is a halogen atom and L is a halogen atom, an alkoxy group having 1 to 5 carbon atoms, an acyloxy group, an alkanesulfonyloxy group or an arenesulfonyloxy group, to a coupling reaction to obtain the 7-methyl-3-methylene-7-octenyl halide of Formula (3):

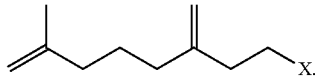
(3)

2. A method for producing 7-methyl-3-methylene-7-octenyl propionate, comprising the steps of:
subjecting a nucleophile of Formula (1):

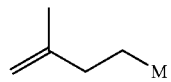
(1)

wherein M is Li, MgQ, Cu, CuQ or CuLiQ, wherein Q is a halogen atom or a 3-methyl-3-butenyl group and an electrophile of Formula (2):

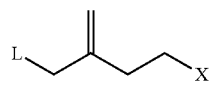
(2)

wherein X is a halogen atom and L is a halogen atom, an alkoxy group having 1 to 5 carbon atoms, an acyloxy group, an alkanesulfonyloxy group or an arenesulfonyloxy group, to a coupling reaction to obtain a 7-methyl-3-methylene-7-octenyl halide of Formula (3):

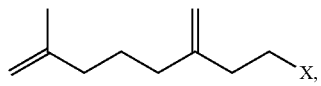
(3)

and
subjecting the 7-methyl-3-methylene-7-octenyl halide (3) to a propionyloxylation reaction to obtain the 7-methyl-3-methylene-7-octenyl propionate of Formula (4):

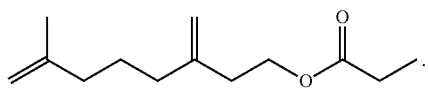
(4)

3. A 7-methyl-3-methylene-7-octenyl halide of Formula (3):

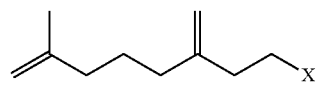
(3)

wherein X is a halogen atom.

4. The 7-methyl-3-methylene-7-octenyl halide of claim 3, wherein the halogen atom is chlorine.

5. The 7-methyl-3-methylene-7-octenyl halide of claim 3, wherein the halogen atom is bromine.

6. The 7-methyl-3-methylene-7-octenyl halide of claim 3, wherein the halogen atom is iodine.

* * * * *